United States Patent [19]

Schallner et al.

[11] Patent Number: 5,288,694

[45] Date of Patent: Feb. 22, 1994

[54] N-ARYL-NITROGEN HETEROCYCLES

[75] Inventors: Otto Schallner, Monheim; Klaus Lürssen, Bergisch Gladbach; Hans-Joachim Santel, Leverkusen; Robert R. Schmidt, Bergisch Gladbach; Renate Vosswinkel, Kürten-Bechen, all of Fed. Rep. of Germany

[73] Assignee: Bayer Atkiengesellschaft, Leverkusen, Fed. Rep. of Germany

[21] Appl. No.: 979,758

[22] Filed: Nov. 23, 1992

[30] Foreign Application Priority Data

Dec. 2, 1991 [DE] Fed. Rep. of Germany ....... 4139636

[51] Int. Cl.$^5$ ..................... A01N 43/36; A01N 43/38; C07D 207/448
[52] U.S. Cl. .................................. 504/166; 504/286; 504/287; 548/476; 548/549
[58] Field of Search ................ 548/476, 549; 504/166, 504/287, 286

[56] References Cited

FOREIGN PATENT DOCUMENTS 0338987 10/1989 European Pat. Off. .
3819439 12/1989 Fed. Rep. of Germany .
3735168 4/1990 Fed. Rep. of Germany .
3839480 5/1990 Fed. Rep. of Germany .
2071100 9/1981 United Kingdom .

OTHER PUBLICATIONS

Patent Abstracts of Japan, vol. 6, No. 85 (C-103) May 22, 1982 Abstract No. JP 810060071.

*Primary Examiner*—Robert W. Ramsuer
*Assistant Examiner*—Jacqueline Haley
*Attorney, Agent, or Firm*—Sprung Horn Kramer & Woods

[57] ABSTRACT

The invention relates to new N-aryl-nitrogen heterocycles of the general formula (I)

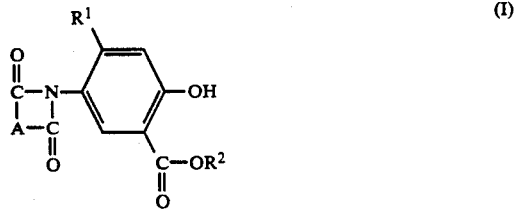

in which
$R^1$ represents hydrogen or halogen,
$R^2$ represents hydrogen or an in each case optionally substituted, straight-chain or branched radical from the series comprising alkyl, alkenyl or cycloalkyl and
A represents one of the radicals or

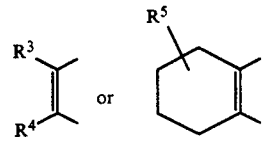

where
$R^3$ represents alkyl,
$R^4$ represents alkyl and
$R^5$ represents hydrogen or alkyl, a plurality of processes for their preparation, and their use as herbicides.

12 Claims, No Drawings

N-ARYL-NITROGEN HETEROCYCLES

The invention relates to new N-aryl-nitrogen heterocycles, a plurality of processes for their preparation, and their use as herbicides.

It has been disclosed that certain N-aryl-nitrogen heterocycles such as, for example, the compound 4-chloro-1-(4-cyano-2-fluoro-5-methoxycarbonylmethylthio-phenyl) -3,5-dimethyl-pyrazole, have herbicidal properties (cf., for example, DE 3,839,480). However, further N-arylnitrogen heterocycles which act as herbicides are also described in DE 3,835,168 and DE 3,819,439.

However, the herbicidal activity of these previously known compounds against problem weeds and their compatibility with important crop plants are not entirely satisfactory in all fields of application.

New N-aryl-nitrogen heterocycles of the general formula (I)

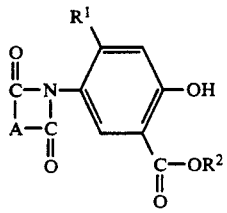

in which
$R^1$ represents hydrogen or halogen,
$R^2$ represents hydrogen or an in each case optionally substituted, straight-chain or branched radical from the series comprising alkyl, alkenyl or cycloalkyl and
A represents one of the radicals

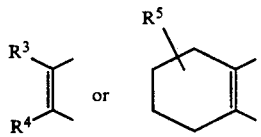

where
$R^3$ represents alkyl,
$R^4$ represents alkyl and
$R^5$ represents hydrogen or alkyl,
have been found.

Depending on the nature of the substituents, the compounds of the formula (I) may exist in the form of geometric and/or optical isomers or isomer mixtures of various compositions. The invention claims the pure isomers as well as the isomer mixtures.

Furthermore, it has been found that the new N-aryl-nitrogen heterocycles of the general formula (I)

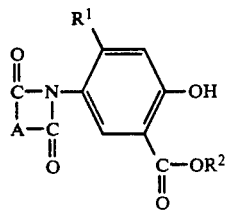

in which
$R^1$ represents hydrogen or halogen,
$R^2$ represents hydrogen or an in each case optionally substituted, straight-chain or branched radical from the series comprising alkyl, alkenyl or cycloalkyl and
A represents one of the radicals

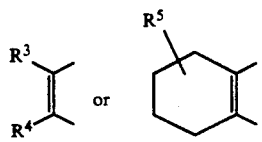

where
$R^3$ represents alkyl,
$R^4$ represents alkyl and
$R^5$ represents hydrogen or alkyl,
are obtained when
a) anhydrides of the formula (II)

in which
A has the abovementioned meaning
are reacted with aniline derivatives of the formula (III)

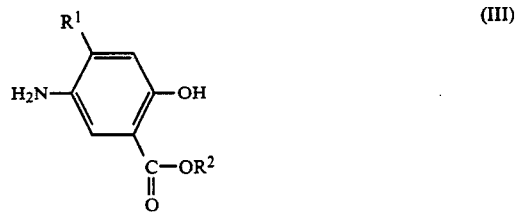

in which
$R^1$ and $R^2$ have the abovementioned meaning,
if appropriate in the presence of a diluent and, if appropriate,
b) the resulting N-aryl-nitrogen heterocycles of the formula (Ia)

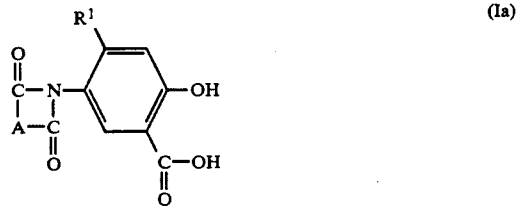

in which
$R^1$ and A have the abovementioned meaning,
are subsequently esterified with alcohols of the formula (V)

(IV)

in which
$R^{2-1}$ represents an in each case optionally substituted radical from the series comprising alkyl, alkenyl or cycloalkyl, if appropriate in the presence of a diluent and in the presence of a reaction auxiliary.

Finally, it has been found that the new N-aryl-nitrogen heterocycles of the general formula (I) have herbicidal properties.

Surprisingly, the N-aryl-nitrogen heterocycles of the general formula (I) according to the invention show a considerably better herbicidal activity against problem weeds, combined with an equally good compatibility with important crop plants, than the N-aryl-nitrogen heterocycles which are known from the prior art such as, for example, the compound 4-chloro-1-(4-cyano-2-fluoro-5-methoxycarbonylmethylthiophenyl)-3,5-dimethyl -pyrazole, which are similar compounds chemically and from the point of view of their action.

Formula (I) provides a general definition of the N-arylnitrogen heterocycles according to the invention. Preferred compounds of the formula (I) are those in which $R^1$ represents hydrogen, fluorine, chlorine, bromine or iodine, $R^2$ represents hydrogen or a straight-chain or branched radical from the series comprising alkyl having 1 to 12 carbon atoms, halogenoalkyl having 1 to 6 carbon atoms and 1 to 13 identical or different halogen atoms, alkoxyalkyl, alkoxyalkoxyalkyl or alkoxycarbonylalkyl, each of which has 1 to 6 carbon atoms in the individual alkyl moieties, alkenyl having 2 to 6 carbon atoms, or cycloalkyl which has 3 to 8 carbon atoms and which is optionally monosubstituted or polysubstituted by identical or different straight-chain or branched alkyl substituents having 1 to 4 carbon atoms, and A represents one of the radicals

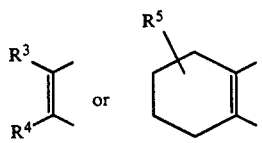

where $R^3$ represents straight-chain or branched alkyl having 1 to 6 carbon atoms, $R^4$ represents straight-chain or branched alkyl having 1 to 6 carbon atoms and $R^5$ represents hydrogen or straight-chain or branched alkyl having 1 to 6 carbon atoms.

Particularly preferred compounds of the formula (I) are those in which $R^1$ represents hydrogen, fluorine, chlorine or bromine, $R^2$ represents hydrogen or a straight-chain or branched radical from the series comprising alkyl having 1 to 8 carbon atoms, halogenoalkyl having 1 to 4 carbon atoms and 1 to 9 identical or different halogen atoms, alkoxyalkyl, alkoxyalkoxyalkyl or alkoxycarbonylalkyl, each of which has 1 to 4 carbon atoms in the individual alkyl moieties, alkenyl having 2 to 4 carbon atoms, or cycloalkyl which has 3 to 7 carbon atoms and which is optionally monosubstituted to trisubstituted by identical or different straight-chain or branched alkyl substituents having 1 to 3 carbon atoms, and A represents one of the radicals

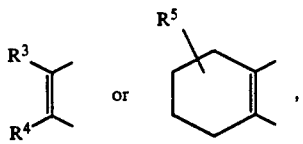

where $R^3$ represents straight-chain or branched alkyl having 1 to 4 carbon atoms, $R^4$ represents straight-chain or branched alkyl having 1 to 4 carbon atoms and $R^5$ represents hydrogen or straight-chain or branched alkyl having 1 to 4 carbon atoms.

Very particularly preferred compounds of the formula (I) are those in which $R^1$ represents hydrogen or fluorine, $R^2$ represents hydrogen or an in each case optionally straight-chain or branched radical from the series comprising alkyl having 1 to 6 carbon atoms, halogenoalkyl having 1 to 3 carbon atoms and 1 to 7 identical or different halogen atoms, alkoxyalkyl, alkoxyalkoxyalkyl or alkoxycarbonylalkyl, each of which has 1 to 3 carbon atoms in the individual alkyl moieties, alkenyl having 2 to 3 carbon atoms, or cyclopropyl, cyclopentyl or cyclohexyl, each of which is optionally monosubstituted or disubstituted by methyl, A represents one of the radicals

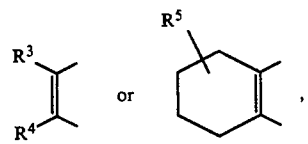

where $R^3$ represents methyl, $R^4$ represents methyl and $R^5$ represents hydrogen, methyl or ethyl.

If, for example, 3,4,5,6-tetrahydrophthalic anhydride and 3-ethoxycarbonyl-4-hydroxy-aniline are used as starting materials, the course of the reaction of process (a) according to the invention can be represented by the following equation:

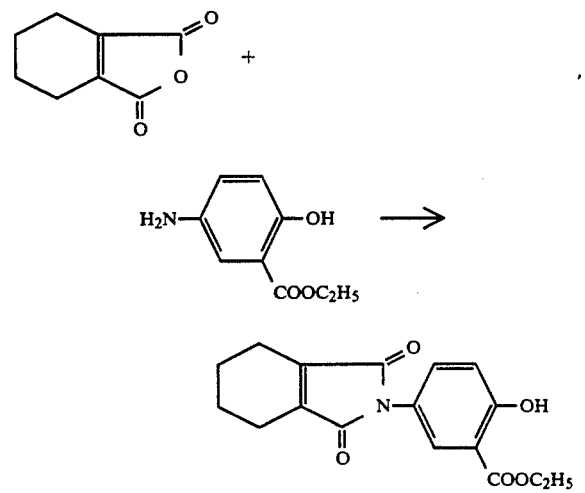

If, for example, 2-hydroxy-5-(2,5-dioxo-3,4-dimethyl-3-pyrrolin-1-yl)-benzoic acid and ethoxyethanol are used as starting materials and oxalyl chloride as reaction auxiliary, the course of the reaction of process (b) according to the invention can be represented by the following equation:

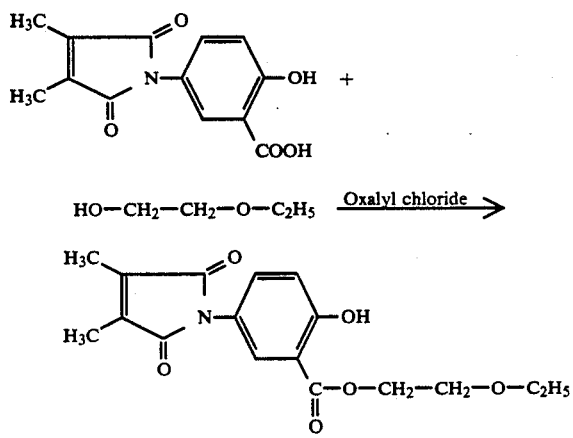

Formula (II) provides a general definition of the anhydrides required as starting materials for carrying out process (a) according to the invention. In this formula (II), A preferably represents those radicals which have already been mentioned in connection with the description of the compounds of the formula (I) according to the invention as being preferred for this substituent. The anhydrides of the formula (II) are generally known (cf., for example, Gazz. Chim. Ital. 57, 300–311 [1927]).

Formula (III) provides a general definition of the aniline derivatives furthermore required as starting materials for carrying out process (a) according to the invention. In this formula (III), R¹ and R² preferably represent those radicals which have already been mentioned in connection with the description of the compounds of the formula (I) according to the invention as being preferred for these substituents.

The aniline derivatives of the formula (III) are also generally known (cf., for example, EP 114,734; U.S. Pat. No. 4,036,951; Collect. Czech. Commun. 29, 730 [1964]).

Formula (Ia) provides a general definition of the N-arylnitrogen heterocycles required as educts for carrying out process (b) according to the invention. In this formula (Ia), R¹ and A preferably represent those radicals which have already been mentioned in connection with the description of the substances of the formula (I) according to the invention as being preferred for these substituents.

The N-aryl-nitrogen heterocycles of the formula (Ia) are compounds according to the invention and can be obtained with the aid of process (a) according to the invention.

Formula (IV) provides a general definition of the alcohols furthermore required as educts for carrying out process (b) according to the invention. In this formula (IV), $R^{2-1}$ preferably represents those radicals which have already been mentioned in connection with the description of the substances of the formula (I) according to the invention as being preferred for the substituent $R^2$, with the exception of the hydrogen radical.

The alcohols of the formula (IV) are generally known compounds of organic chemistry.

Suitable diluents for carrying out process (a) according to the invention are inert organic solvents These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether; ketones such as acetone or butanone or methyl isobutyl ketone; nitriles such as acetonitrile, propionitrile or benzonitrile; amides such as N,N-dimethylformam.ide, N,N-dimethylacetamide, N-methylformanilide, N-methylpyrrolidone or hexamethylphosphoric triamide, esters such as methyl acetate or ethyl acetate, or sulphoxides such as dimethyl sulphoxide.

If appropriate, process (a) according to the invention can be carried out in the presence of a suitable reaction auxiliary. Reaction auxiliaries which are preferably used are inorganic or organic acids such as, for example, acetic acid or p-toluenesulphonic acid, anhydrides such as acetic anhydride, or acid chlorides such as acetyl chloride. It is also possible to use other customary water-eliminating agents such as, for example, N,N'-dicyclohexylcarbodiimide, as reaction auxiliaries. Moreover, it is also possible to use a suitable excess of the acids which are used as reaction auxiliaries simultaneously as the diluent.

When carrying out process (a) according to the invention, the reaction temperatures can be varied within a substantial range. In general, the process is carried out at temperatures between 20° C. and 180° C., preferably at temperatures between 50° C. and 150° C.

Process (a) according to the invention is customarily carried out under atmospheric. However, it is also possible to carry out the process under increased or reduced pressure For carrying out process (a) according to the invention, 0.8 to 1.5 moles, preferably 1.0 to 1.2 moles, of aniline derivative of the formula (III) and, if appropriate, 0.5 to 15.0 moles of reaction auxiliary are generally employed per mole of anhydride of the formula (II). The reaction is carried out and the reaction products are worked up and isolated by known processes (cf. in this context, for example, DE 3,712,987 or the preparation examples).

Suitable diluents for carrying out process (b) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate, or sulphoxides such as dimethyl sulphoxide.

If appropriate, process (b) according to the invention can be carried out in the presence of a suitable reaction auxiliary. Suitable reaction auxiliaries are customary acid halide formers such as thionyl chloride, sulphuryl chloride, phosphorus trichloride, phosphorus pentachloride, phosphorus oxychloride or oxalyl chloride.

When carrying out process (b) according to the invention, the reaction temperatures can be varied within a substantial range. In general, the process is carried out at temperatures between 0° C. and 80° C., preferably at temperatures between 20° C. and 50° C.

For carrying out process (b) according to the invention, 1.0 to 10.0 moles, preferably 1.0 to 5.0 moles, of alcohol of the formula (IV) and, if appropriate, 1.0 to 3.0 moles, preferably 0.5 to 2.0 moles, of reaction auxiliary are generally employed per mole of N-arylnitrogen heterocycle of the formula (Ia).

The reaction is carried out and the reaction products are worked up and isolated by known processes (cf. also the preparation examples).

The end products of the formula (I) are purified with the aid of customary processes, for example by column chromatography or by recrystallisation. They are characterised with the aid of the melting point or, in the case of noncrystallising compounds, with the aid of proton nuclear resonance spectroscopy ($^1$H NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

In this context, the active compounds according to the invention can be employed with particular success for combating monocotyledon and dicotyledon weeds in monocotyledon and dicotyledon cultures such as, for example, wheat, barley, oil seed rape or soya beans.

In addition, the active compounds according to the invention also engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amount of active compound applied to the plants or their environment and the way in which the compounds are applied. In each case, growth regulators are intended to influence the crop plants in the particular manner desired.

The amount of leaf on plants can be controlled, under the influence of growth regulators, so that defoliation of the plants at a desired point in time is achieved Such defoliation is of great importance in the mechanical harvesting of cotton, but is also of interest for facilitating harvesting in other crops such as, for example, in viticulture. Defoliation of the plants can also be carried out to lower the transpiration before they are transplanted.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. Suitable liquid solvents are in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

Suitable solid carriers are: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; suitable emulsifying and/or foam-forming agents are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysis products; suitable dispersing agents are: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazo-sulfuron-ethyl, thifensulfuron-methyl, triasulfuron and tribenuronmethyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range It depends essentially on the nature of the desired effect In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

Example 1

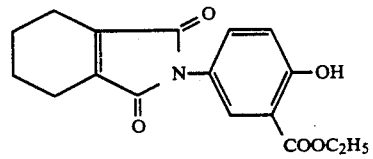

(Process (a))

6.4 g (0.042 mol) of 3,4,5,6-tetrahydrophthalic anhydride are added to a solution of 7.3 g (0.04 mol) of methyl 5-amino-2-hydroxybenzoate (cf., for example, EP 114,734) in 100 ml of glacial acetic acid, and the mixture is stirred for 16 hours at 80° C. to 85° C. For working-up, the cooled reaction mixture is concentrated in vacuo, the residue is taken up in 150 ml of dichloromethane, and the mixture is washed with saturated sodium hydrogen carbonate solution and water, dried over sodium sulphate and again concentrated in vacuo. The residue is stirred with petroleum ether, filtered off and dried.

10.5 g (83% of theory) of N-(3-ethoxycarbonyl-4-hydroxyphenyl)-3,4,5,6-tetrahydrophthalimide of melting point 90° C. are obtained.

Example 2

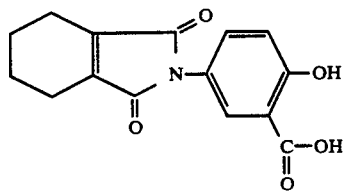

(Process (a))

22.8 g (0.15 mol) of 3,4,5,6-tetrahydrophthalic anhydride are added to 24.6 g (0.15 mol; 93% strength) of 5-amino-2-hydroxy-benzoic acid in 240 ml of glacial acetic acid, and the mixture is refluxed for 12 to 16 hours, with stirring. For working-up, the cooled reaction mixture is concentrated in vacuo, the residue is stirred with 360 ml of a mixture of petroleum ether and ethyl acetate (30:1), and the crystalline product is filtered off with suction and dried.

41 g (95% of theory) of N-(3-hydroxycarbonyl-4-hydroxyphenyl)-3,4,5,6-tetrahydrophthalimide of melting point 240° C. are obtained.

Example 3

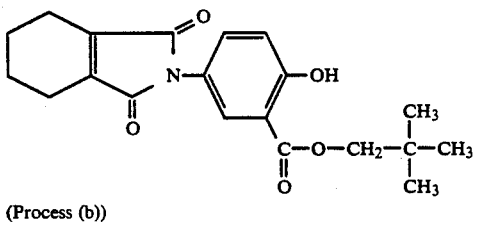

(Process (b))

1.4 g (0.011 mol) of oxalyl chloride are added to 2.9 g (0.01 mol) of N-(5-hydroxycarbonyl-4-hydroxyphenyl)-3,4,5,6-tetrahydrophthalimide in 50 ml of dry dichloromethane, and the mixture is stirred at room temperature until the evolution of gas has ceased (approx. 30 hours). The resulting solution is freed from solvent in vacuo, the residue is suspended in 80 ml of carbon tetrachloride, 0.9 g (0.01 mol, 98% strength) 2,2-dimethyl-1-propanol are added, and the mixture is refluxed for 16 hours. For working-up, the cooled reaction mixture is washed in succession with water and saturated sodium hydrogen carbonate solution, dried over magnesium sulphate and again concentrated in vacuo.

3.2 g (90% of theory) of N-[3-(2,2-dimethyl-1-propyloxycarbonyl)-4-hydroxyphenyl]-3,4,5,6-tetrahydrophthalimide are obtained as an oil.

$^1$H NMR (CDCl$_3$/tetrasilylmethane):
δ=1.03 (s, 9H); 1.83 (m, 4H); 2.43 (m, 4H); 4.05 (s, 2H); 7.06 (d, 1H); 7.40 (m, 1H); 7.85 (d, 1H) ppm The following N-aryl-nitrogen heterocycles of the general formula (I)

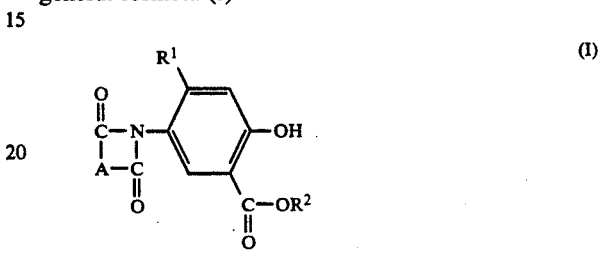

are obtained in analogous manner and following the general preparation instructions:

| Example No. | Structure | R$^1$ | R$^2$ | physical properties |
|---|---|---|---|---|
| 4 | (tetrahydrophthalimide) | H | —CH(CH$_3$)$_2$ | $^1$H-NMR*): 7,05(d, 1H) |
| 5 | (tetrahydrophthalimide) | H | —CH$_2$—CH$_2$—CH$_3$ | m.p.: 75° C. |
| 6 | (tetrahydrophthalimide) | H | —CH$_2$—CH(CH$_3$)$_2$ | m.p.: 67° C. |
| 7 | (tetrahydrophthalimide) | H | —CH(CH$_3$)—CH$_2$<br>          \|<br>          CH$_3$ | $^1$H-NMR*): 7,05(d, 1H) |
| 8 | (tetrahydrophthalimide) | H | —C(CH$_3$)$_3$ | m.p.: 108° C. |

-continued

| Example No. | [structure with C(=O)-N-A-C(=O)] | R¹ | R² | physical properties |
|---|---|---|---|---|
| 9 | [cyclohexene-fused imide] | H | [cyclopentyl-methyl] | m.p.: 102° C. |
| 10 | [cyclohexene-fused imide] | H | CH₃ | m.p.: 137° C. |
| 11 | [dimethyl maleimide, H₃C/H₃C] | H | CH₃ | m.p.: 148° C. |

*)The ¹H NMR spectra were recorded in deuterochloroform (CDCl₃) using tetramethylsilane (TMS) as internal standard. The chemical shift is given as the δ-value in ppm.

USE EXAMPLES

In the Use Examples which follow, the compound listed below was employed as comparison substance:

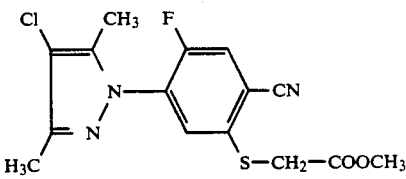

(A)

(cf., for example, DE 3,839,480)

Example A

Pre-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

A clearly superior activity and crop plant selectivity compared with the prior art is shown, in this test, for example by the compounds of Preparation Example 1.

Example B

Post-emergence test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area.

After three weeks, the degree of damage to the plants is rated in % damage in comparison to the development of the untreated control. The figures denote:

0% = no action (like untreated control)
100% = total destruction

A clearly superior activity and crop plant selectivity compared with the prior art is shown, in this test, for example by the compounds of Preparation Example 1.

It will be understood that the specification and examples are illustrative but not limitative of the present invention and that other embodiments within the spirit and scope of the invention will suggest themselves to those skilled in the art.

What is claimed is:

1. An N-aryl-nitrogen heterocycle of the formula

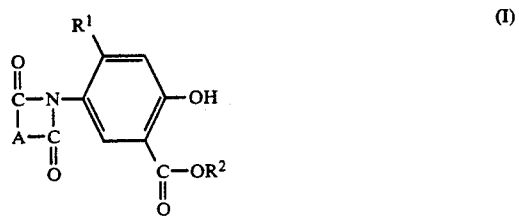

(I)

wherein
R¹ represents hydrogen, fluorine, chlorine, bromine or iodine,
R² represents hydrogen or a straight-chain or branched radical selected from the group consisting of alkyl, halogenoalkyl having identical or different halogen atoms, alkoxyalkyl, alkoxyalkoxyalkyl, alkoxycarbonylalkyl, alkenyl, or cycloalkyl which is optionally monosubstituted or polysubstituted by identical or different straight-chain or branched alkyl substituents and
A represents one of the radicals

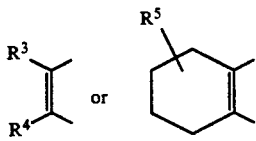

where
R³ represents straight-chain or branched alkyl,
R⁴ represents straight-chain or branched alkyl,
R⁵ represents hydrogen or straight-chain or branched alkyl.

2. An N-aryl-nitrogen heterocycle according to claim 1 wherein
R¹ represents hydrogen, fluorine, chlorine, bromine or iodine,
R¹ represents hydrogen or a straight-chain or branched radical selected from the group consisting of alkyl having 1 to 12 carbon atoms, halogenoalkyl having 1 to 6 carbon atoms and 1 to 13 identical or different halogen atoms, alkoxyalkyl, alkoxyalkoxyalkyl or alkoxycarbonylalkyl, each of which has 1 to 6 carbon atoms in the individual alkyl moieties, alkenyl having 2 to 6 carbon atoms, or cycloalkyl which has 3 to 8 carbon atoms and which is optionally monosubstituted or polysubstituted by identical or different straight-chain or branched alkyl substituents having 1 to 4 carbon atoms, and
A represents one of the radicals

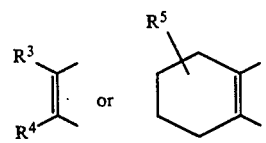

where
R³ represents straight-chain or branched alkyl having 1 to 6 carbon atoms,
R⁴ represents straight-chain or branched alkyl having 1 to 6 carbon atoms and
R⁵ represents hydrogen or straight-chain or branched alkyl having 1 to 6 carbon atoms.

3. An N-aryl-nitrogen heterocycle according to claim 1, wherein
R¹ represents hydrogen, fluorine, chlorine or bromine,
R² represents hydrogen or a straight-chain or branched radical selected from the group consisting of alkyl having 1 to 8 carbon atoms, halogenoalkyl having 1 to 4 carbon atoms and 1 to 9 identical or different halogen atoms, alkoxyalkyl, alkoxyalkoxyalkyl or alkoxycarbonylalkyl, each of which has 1 to 4 carbon atoms in the individual alkyl moieties, alkenyl having 2 to 4 carbon atoms, or cycloalkyl which has 3 to 7 carbon atoms and which is optionally monosubstituted to trisubstituted by identical or different straight-chain or branched alkyl substituents having 1 to 3 carbon atoms, and
A represents one of the radicals

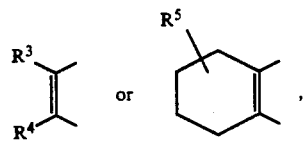

where
R³ represents straight-chain or branched alkyl having 1 to 4 carbon atoms,
R⁴ represents straight-chain or branched alkyl having 1 to 4 carbon atoms and
R⁵ represents hydrogen or straight-chain or branched alkyl having 1 to 4 carbon atoms.

4. An N-Aryl-nitrogen heterocycle according to claim 1, wherein
R¹ represents hydrogen or fluorine,
R² represents hydrogen or an in each case optionally straight-chain or branched radical selected from the group consisting of alkyl having 1 to 6 carbon atoms, halogenoalkyl having 1 to 3 carbon atoms and 1 to 7 identical or different halogen atoms, alkoxyalkyl, alkoxyalkoxyalkyl or alkoxycarbonylalkyl, each of which has 1 to 3 carbon atoms in the individual alkyl moieties, alkenyl having 2 to 3 carbon atoms, or cyclopropyl, cyclopentyl or cyclohexyl, each of which is optionally monosubstituted or disubstituted by methyl,
A represents one of the radicals

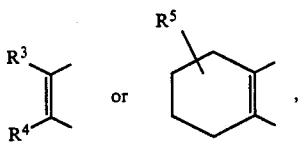

where
R¹ represents methyl,
R⁴ represents methyl and
R⁵ represents hydrogen, methyl or ethyl.

5. A compound according to claim 1 wherein such compound is
N-(3-ethoxycarbonyl-4-hydroxyphenyl)-3,4,5,6-tetrahydrophthalimide of the formula

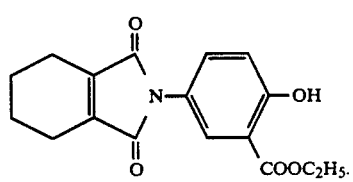

6. A compound according to claim 1 wherein such compound is
N-3-(isopropoxycarbonyl-4-hydroxyphenyl)-3,4,5,6-tetrahydrophthalimide of the formula

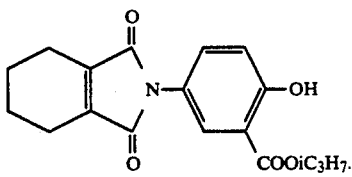

7. A compound according to claim 1 wherein such compound is
N-3(tert.-butoxycarbonyl-4-hydroxyphenyl)-3,4,5,6-tetrahydrophthalimide of the formula

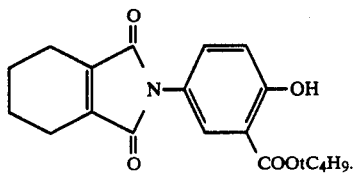

8. A herbicidal composition comprising a herbicidally effective amount of a compound according to claim 1 and a diluent.

9. A method of combating unwanted vegetation which comprises applying to such vegetation or to a locus from which it is desired to exclude such vegetation a herbicidally effective amount of a compound according to claim 1.

10. A method according to claim 9, wherein such compound is
N-(3-ethoxycarbonyl-4-hydroxyphenyl)-3,4,5,6-tetrahydrophthalimide
N-(3-isopropoxycarbonyl-4-hydroxyphenyl)-3,4,5,6-tetrahydropthalimide
N-(3-tert.-butoxycarbonyl-4-hydroxyphenyl)-3,4,5,6-tetrahydrophthalimide.

11. An N-aryl-nitrogen heterocycle of the formula (Ia)

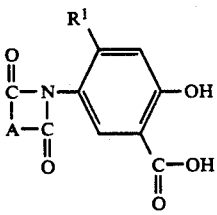

wherein
$R^1$ represents hydrogen or halogen,
A represents one of the radicals

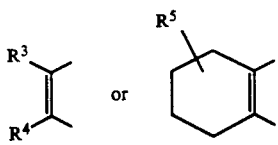

where
$R^3$ represents alkyl,
$R^4$ represents alkyl and
$R^5$ represents hydrogen or alkyl.

12. An N-aryl-nitrogen heterocycle according to claim 11, wherein in that.
$R^1$ represents hydrogen, fluorine, chlorine, bromine or iodine,
A represents one of the radicals

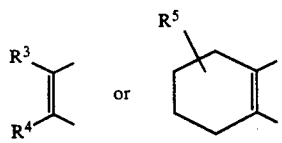

where
$R^3$ represents straight-chain or branched alkyl having 1 to 6 carbon atoms,
$R^4$ represents straight-chain or branched alkyl
$R^5$ represents hydrogen or straight-chain or branched alkyl having 1 to 6 carbon atoms.

* * * * *

UNITED STATES PATENT AND TRADEMARK OFFICE
CERTIFICATE OF CORRECTION

PATENT NO.   : 5,288,694
DATED        : February 22, 1994
INVENTOR(S)  : Otto Schallner, et al.

It is certified that error appears in the above-indentified patent and that said Letters Patent is hereby corrected as shown below:

Column 15, line 29,    cancel "$R^1$" and substitute --$R^2$--.

Column 16, line 47,    cancel "$R^1$" and substitute --$R^3$--.

Signed and Sealed this

Twenty-third Day of March, 1999

Attest:

Q. TODD DICKINSON

Attesting Officer    Acting Commissioner of Patents and Trademarks